(12) United States Patent
Kuwayama et al.

(10) Patent No.: US 12,342,811 B2
(45) Date of Patent: Jul. 1, 2025

(54) INSTRUMENT FOR USE IN OPERATING CELL

(71) Applicant: ADVANCED INSTITUTE OF REPRODUCTIVE TECHNOLOGIES, Tokyo (JP)

(72) Inventors: Masashige Kuwayama, Tokyo (JP); Rio Kuwayama, Tokyo (JP)

(73) Assignee: ADVANCED INSTITUTE OF REPRODUCTIVE TECHNOLOGIES, Tokyo (JP)

( * ) Notice: Subject to any disclaimer, the term of this patent is extended or adjusted under 35 U.S.C. 154(b) by 751 days.

(21) Appl. No.: 17/596,667

(22) PCT Filed: Nov. 27, 2019

(86) PCT No.: PCT/JP2019/046348
§ 371 (c)(1),
(2) Date: Dec. 16, 2021

(87) PCT Pub. No.: WO2020/255444
PCT Pub. Date: Dec. 24, 2020

(65) Prior Publication Data
US 2022/0304298 A1 Sep. 29, 2022

(30) Foreign Application Priority Data
Jun. 19, 2019 (JP) .................................. 2019-113807

(51) Int. Cl.
*A01N 1/146* (2025.01)
*B01L 3/00* (2006.01)
*C12M 3/00* (2006.01)

(52) U.S. Cl.
CPC ............ *A01N 1/146* (2025.01); *B01L 3/5085* (2013.01); *C12M 21/06* (2013.01)

(58) Field of Classification Search
None
See application file for complete search history.

(56) References Cited

U.S. PATENT DOCUMENTS 5,916,526 A * 6/1999 Robbins ................ B01L 3/5085
422/549
2009/0011947 A1* 1/2009 Ozawa ............... G01N 21/6452
506/9

(Continued)

FOREIGN PATENT DOCUMENTS

CN   103842493 A   6/2014
CN   204265762 U   4/2015

(Continued)

OTHER PUBLICATIONS

Office Action issued Apr. 4, 2022 in Indian Application No. 202247000528.

(Continued)

*Primary Examiner* — William H. Beisner
(74) *Attorney, Agent, or Firm* — Sughrue Mion, PLLC (57) ABSTRACT

Provided is an instrument having favorable operability when a plurality of cells is operated. An instrument 1 of the present invention includes a plate main body 2 having a well 8 and is used when cells are operated. The well 8 has a bottom 8A and a curved inner peripheral wall 8B that is formed so as to be contiguous to the bottom 8A, and a plurality of protruding portions 13 for partitioning the bottom 8A and the inner peripheral wall 8B into a plurality of portions is provided along the bottom 8A and the inner peripheral wall 8B. Recesses 13A are formed in partitioned portions of the bottom 8A by forming raised portions 13A such that each of the raised portions 13A extends from one of the protruding portions 13 to the bottom 8A, and cells are settled into the recesses 13A.

9 Claims, 9 Drawing Sheets

(56) References Cited

U.S. PATENT DOCUMENTS

2014/0061972 A1\* 3/2014 Motadel ............... B01L 3/5085
                                                                                        264/322
2014/0212962 A1    7/2014 Inoue
2018/0201888 A1    7/2018 Miwa et al.

FOREIGN PATENT DOCUMENTS

| EP | 3211066 A1 | 8/2017 | |
|---|---|---|---|
| JP | 2000-189155 A | 7/2000 | |
| JP | 2018-000134 A | 1/2018 | |
| WO | WO-9819794 A1 \* | 5/1998 | ............ B01L 3/5085 |
| WO | 2014/061244 A1 | 4/2014 | |
| WO | 2017/047735 A1 | 3/2017 | |
| WO | WO-2017187543 A1 \* | 11/2017 | ........... A01N 1/0221 |
| WO | 2018/180320 A1 | 10/2018 | |

OTHER PUBLICATIONS

Toshiyuki Sugimoto et al., "The state-of-the-art human oocyte/embryo vitrification method: Cryotec method", The 24th Workshop and Academic Conference of the Journal of Clinical Embryologist, Dec. 10, 2018, pp. 120-126.
International Search Report for PCT/JP2019/046348, dated Feb. 18, 2020.

\* cited by examiner

INSTRUMENT FOR USE IN OPERATING CELL

CROSS REFERENCE TO RELATED APPLICATIONS

This application is a National Stage of International Application No. PCT/JP2019/046348 filed Nov. 27, 2019, claiming priority based on Japanese Patent Application No. 2019-113807 filed Jun. 19, 2019.

TECHNICAL FIELD

The present invention relates to an instrument that is used when a cell is operated.

BACKGROUND ART

In recent years, cryopreservation of egg cells and embryos has attracted attention in human fertility treatments. In the related art, as a method of cryopreserving mammalian egg cells or the like, a method of attaching an egg cell, an embryo, or the like that has been immersed in a vitrification solution to the inner surface of a cryopreservation container, such as a vial or a straw, hermetically sealing the cryopreservation container, and rapidly cooling the cryopreservation container by bringing it into contact with liquid nitrogen is known (see, for example, PTL 1).

In addition, a vitrification preservation technique that enables preservation of a fertilized egg with only small damage has been reported by Kuwayama et al. This vitrification preservation technique uses a cell freezing plate that has wells into which an equilibrium solution and a vitrification solution are dispensed.

CITATION LIST

Patent Literature

PTL 1: Japanese Unexamined Patent Application Publication No. 2000-189155

SUMMARY OF INVENTION

Technical Problem

In the case of freezing a fertilized egg, a single fertilized egg is taken out, and a freezing operation is performed by using a single cell freezing plate. However, in the case of freezing a plurality of fertilized eggs, it is necessary to replace the cell freezing plate, the equilibrium solution, and the vitrified solution each time the freezing operation is performed, and such replacement is burdensome.

Accordingly, it is an object of the present invention to provide an instrument having favorable operability when a plurality of cells is operated.

Solution to Problem

An instrument according to the present disclosure includes a main body portion having a first well and is used when cells are operated. The first well has a bottom that is formed in a curved shape and a curved inner peripheral wall that is contiguous to the bottom. A plurality of protruding portions for partitioning the bottom and the inner peripheral wall into a plurality of portions is provided along the bottom and the inner peripheral wall. Recesses are formed in partitioned portions of the bottom by forming raised portions in such a manner that each of the raised portions extends from one of the protruding portions to the bottom, and the cells are settled in the recesses.

In the instrument according to the present disclosure, the protruding portions are each provided in such a manner as to extend from the center of the first well along the bottom and the inner peripheral wall.

In the instrument according to the present disclosure, the bottom partitioned by the protruding portions and the inner peripheral wall partitioned by the protruding portions communicate with each other.

In the instrument according to the present disclosure, the bottom and the inner peripheral wall are each partitioned into four portions by arranging the plurality of the protruding portions in such a manner that the protruding portions cross each other at the center of the bottom.

In the instrument according to the present disclosure, each of the protruding portions has a curved end and an inclined surface that extends from an upper end of the protruding portion to a lower end of the protruding portion.

In the instrument according to the present disclosure, each of the protruding portions has a height of 100 µm to 1,000 µm.

In the instrument according to the present disclosure, the height of each of the protruding portions increases from the inner peripheral wall to the bottom.

In the instrument according to the present disclosure, the main body portion has a second well that is formed adjacent to the first well, and an equilibrium solution and a vitrification solution are respectively injected into the first well and the second well. The protruding portions are formed only in the first well, and the instrument is used at a stage before the cells are frozen.

In the instrument according to the present disclosure, a waste-liquid portion for discarding a liquid injected in the first well or the second well is formed in the main body portion.

Advantageous Effects of Invention

In the instrument according to the present disclosure, the protruding portions are arranged so as to partition the bottom, so that the bottom is divided into a plurality portions. As a result, the single instrument is enough to perform an operation on a plurality of cells, and the cells can be promptly handled. Therefore, the instrument according to the present invention has excellent operability.

In addition, for example, when fertilized eggs or unfertilized eggs are operated, a pretreatment for freezing a plurality of fertilized eggs or a plurality of unfertilized eggs can be performed with a single instrument, and thus, the number of instruments to be discarded, the amount of an equilibrium solution to be discarded, and the amount of a vitrification solution to be discarded can be reduced with certainty.

DESCRIPTION OF EMBODIMENTS

An instrument according to the present embodiment will be described with reference to FIG. 1 to FIG. 7. The instrument can be used when various cells are operated, and in the present embodiment, an instrument that is used at a stage before a fertilized egg cell (such as a blastocyst cell) or an unfertilized egg cell is frozen will be described as an example.

Figure 1:
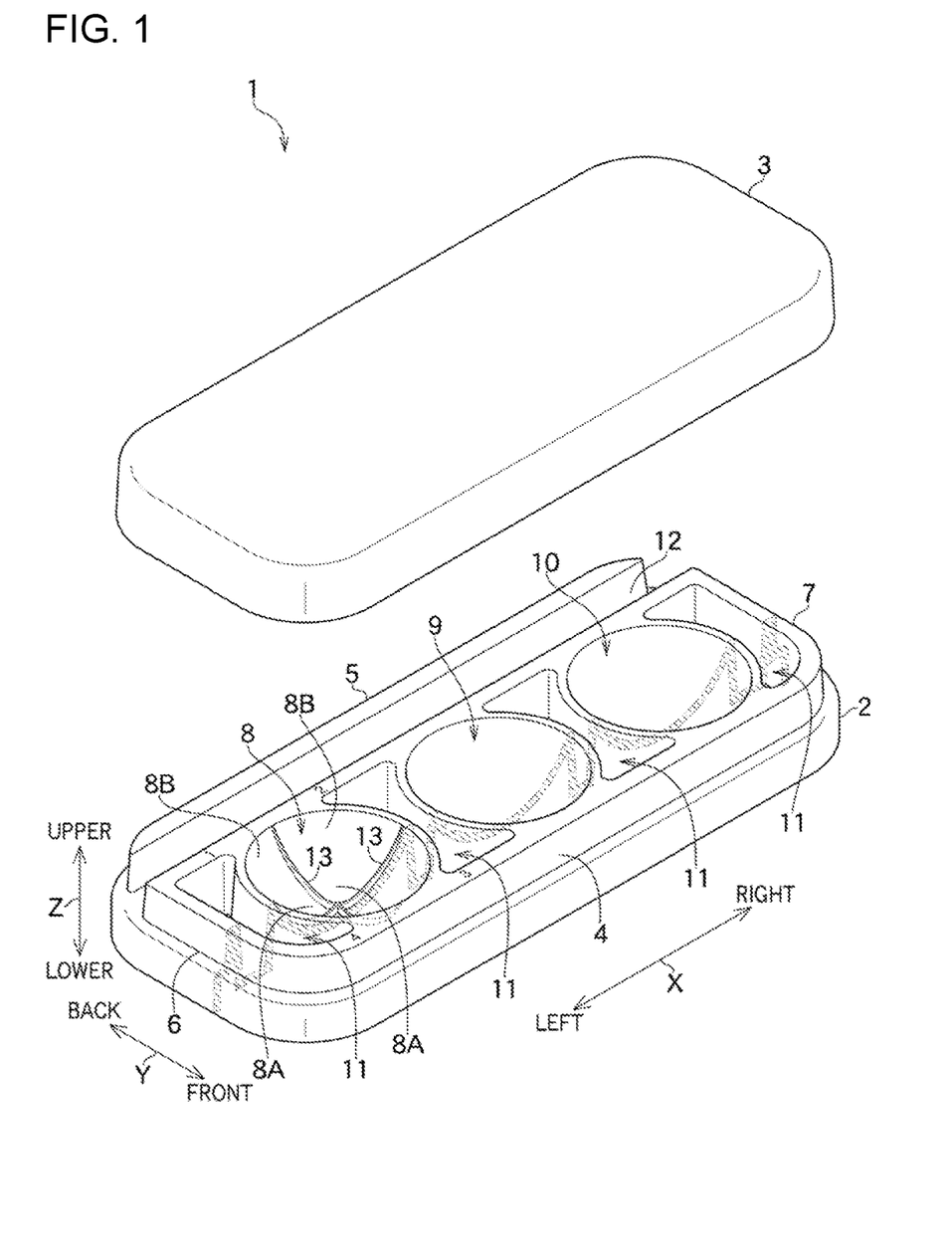
FIG. 1 is a perspective view of an instrument according to an embodiment of the present disclosure.

As illustrated in FIG. 1, an instrument 1 according to the present embodiment includes a plate main body 2 that serves as a main body portion and a cover member 3 that covers the plate main body 2 from above.

The following description is based on FIG. 1, and the longitudinal direction of the plate main body 2 will be referred to as a transverse direction X. The lateral direction of the plate main body 2 will be referred to as a depth direction Y. The height direction of the plate main body 2 will be referred to as a vertical direction Z.

Figure 2:
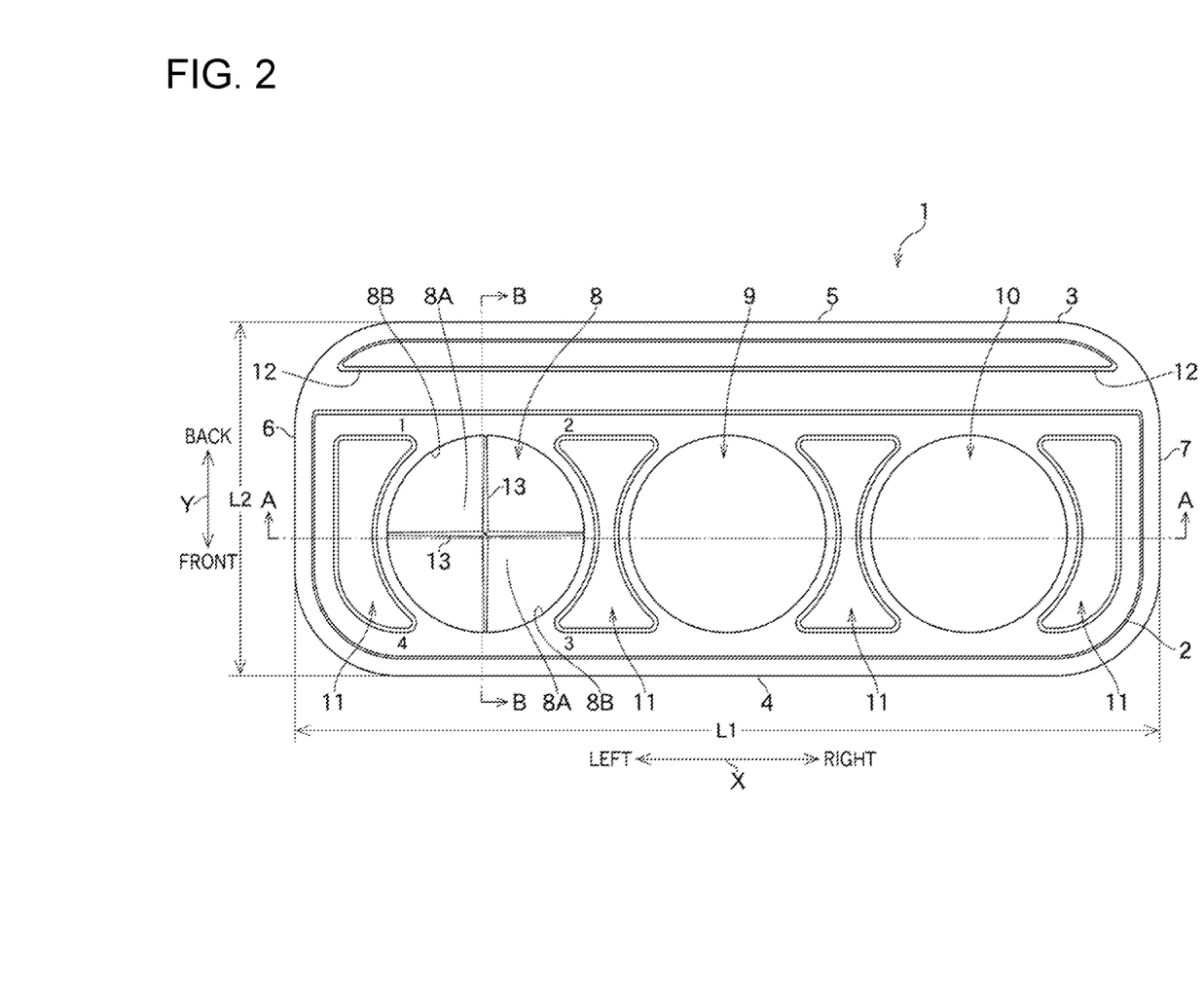
FIG. 2 is a plan view of a main body portion (a plate main body) of the instrument according to the embodiment of the present disclosure.

As illustrated in FIG. 2, the plate main body 2 has a horizontally elongated shape and has a front wall 4, a rear wall 5 that is opposite the front wall 4, a left side wall 6 that is formed so as to be contiguous to the front wall 4 and the rear wall 5, and a right side wall 7 that is formed so as to be contiguous to the front wall 4 and the rear wall 5.

The plate main body 2 is made of a transparent material, which is, for example, polypropylene, a polystyrene, polycarbonate, acrylic, or glass. Regarding the size of the plate main body 2, a length L1 in the transverse direction X is set to 5.5 cm to 7.5 cm, and a length L2 in the depth direction Y is set to 2 cm to 3.5 cm.

Figure 3:
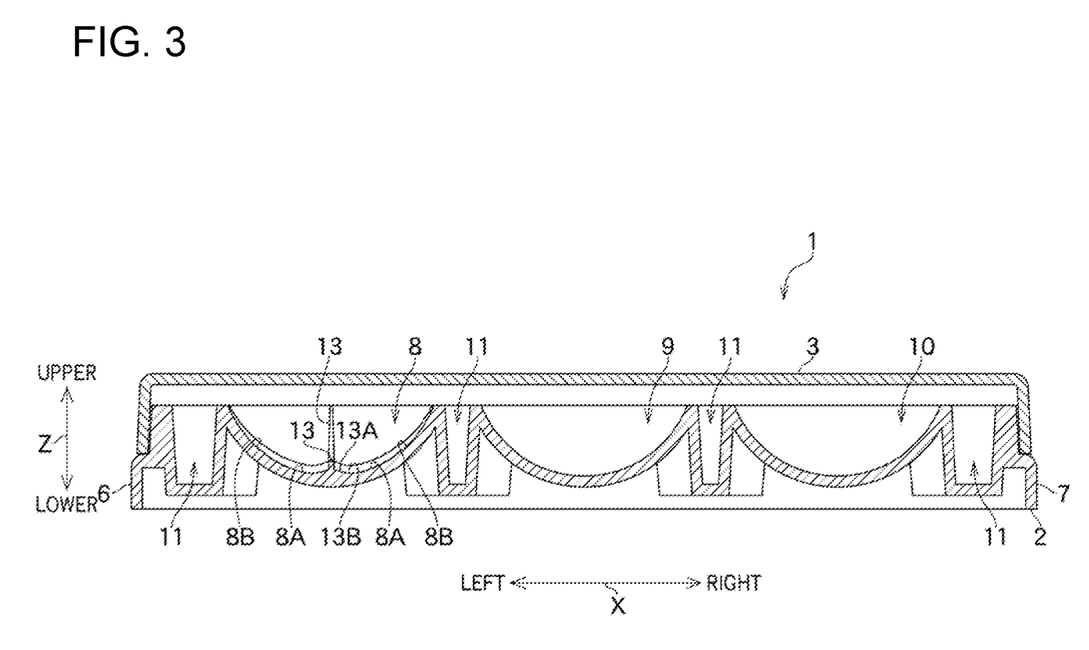
FIG. 3 is a sectional view of the instrument according to the embodiment of the present disclosure taken along line A-A of FIG. 2.

As illustrated in FIG. 3, the plate main body 2 has wells 8 to 10 that are arranged in the transverse direction X and each of which is formed in a substantially hemispherical shape. More specifically, the well (second well) 9 is formed adjacent to the well (first well) 8, and the well (third well) 10 is formed adjacent to the well 9. The diameter and the depth of the well 8 are 1.5 mm and 5 mm, respectively, and the well 9 and the well 10 are each designed so as to have a diameter approximately the same as the diameter of the well 8 and a depth approximately the same as the depth of the well 8.

An equilibrium solution (ES) is injected into the well 8 on the left-hand side, and a vitrification solution (VS) is injected into the well 9 at the center and the well 10 on the right-hand side.

The size of the plate main body 2 is suitably changed in accordance with the size of each of the wells 8 to 10, the number of wells, or the arrangement of the wells. The diameter and the depth of each of the wells 8 to 10 are also suitably changed in accordance with the size or the like of the plate main body 2.

The front surface of the plate main body 2 has recessed waste-liquid portions (recesses for a waste liquid) 11 that are formed between the left side wall 6 and the well 8, between the well 8 and the well 9, between the well 9 and the well 10, and between the well 10 and the right side wall 7 (FIG. 2). Each of the waste-liquid portions 11 is used for discarding the equilibrium solution or the vitrification solution that is no longer necessary. Note that the equilibrium solution and the vitrification solution will be described later.

In addition, a single groove portion 12 is formed behind the wells 8 to 10 so as to extend in the transverse direction X (FIG. 2). A cell freezing tool that has a flat plate-like shape and that is used when a fertilized egg is frozen is placed in the groove portion 12. The number of grooves 12 is not limited to one, and a plurality of grooves 12 may be formed.

Figure 4:
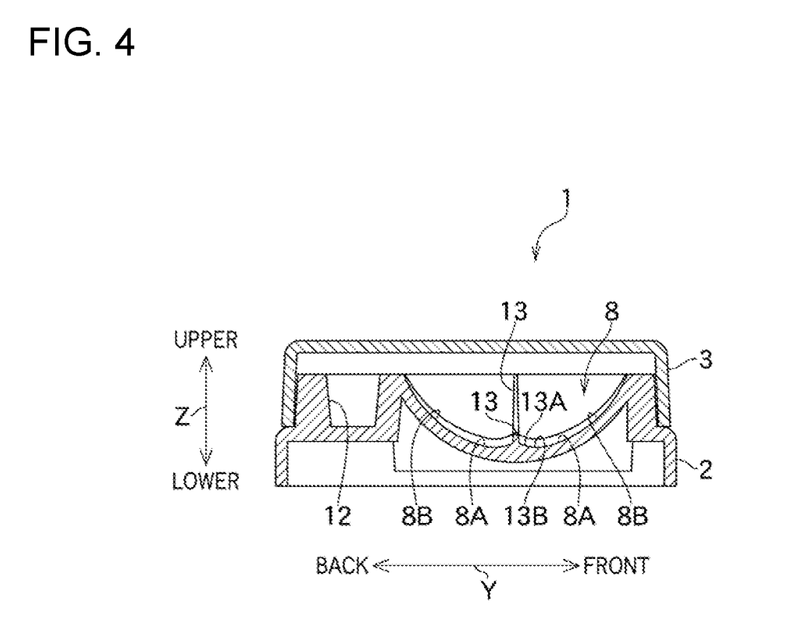
FIG. 4 is a cross-sectional view of the instrument according to the embodiment of the present disclosure taken along line B-B of FIG. 2.

As illustrated in FIG. 4, the well 8 has a curved bottom 8A and a side wall (inner peripheral wall) 8B that is formed so as to be contiguous to the bottom 8A. In the well 8, two protruding portions 13 are formed on the bottom 8A, and these protruding portions 13 are arranged so as to cross each other at 90 degrees at the center of the bottom 8A when viewed in plan view (FIG. 2). Thus, the protruding portions 13 are each formed so as to extend from the center of the bottom 8A along the side wall 8B.

Ends of the protruding portions 13 are each formed in a curved shape, and the protruding portions 13 are each designed to have a height H of 400 μm and a width of 100 μm. It is preferable that the height H of each of the protruding portions 13 be 100 μm to 1,000 μm for ease of operation and in order to prevent a fertilized egg from jumping over the protruding portion 13. In addition, it is preferable that the height H of each of the protruding portions 13 gradually increase from the side wall 8B to the bottom 8A. Note that the height H and the width of each of the protruding portions 13 can be suitably changed.

Numbers (1 to 4) are provided as marks around the well 8 (FIG. 2). By providing these marks, portions of the bottom 8A that are partitioned from one another can be easily distinguished.

Raised portions 13A are formed on the bottom 8A of the well 8 so as to extend to their respective protruding portions 13. By forming the raised portions 13A, in the portions of the bottom 8A partitioned by the protruding portions 13, recesses 13B are formed at positions a short distance away from their respective protruding portions 13.

Since the well 8 is provided with the two protruding portions 13 crossing each other, the bottom 8A is divided into four portions. The number of fertilized eggs that can be left to stand is determined depending on the number of protruding portions 13 provided on the bottom 8A, that is, the number of divided portions of the bottom 8A.

In the present embodiment, although the bottom 8A is divided into the four portions by being partitioned by the two protruding portions 13, the number of the protruding portions 13 is not limited to two and may at least be one or more. Note that the area of each of the partitioned portions of the bottom 8A decreases by increasing the number of the protruding portions 13, and the operability may be impaired. Thus, it is most preferable to divide the bottom 8A into four portions.

Next, a method of using the instrument 1 according to the present embodiment in the case of freezing four fertilized eggs will be described.

First, 300 µl of the equilibrium solution is dispensed into the well 8, and 300 µl of the vitrification solution is dispensed into each of the wells 9 and 10.

Here, the vitrification solution is a solution containing a cryoprotectant that is necessary for vitrification of a cell, and the equilibrium solution is a solution containing a cryoprotectant such that the concentration of the cryoprotectant contained in the equilibrium solution is lower than the concentration of the cryoprotectant contained in the vitrification solution. Both of these solutions are adjusted so as to have a composition that reduces damage to fertilized eggs.

After dispensing the equilibrium solution and the vitrification solution, a fertilized egg is put into the well 8 in such a manner as to be settled on one of the four portions of the bottom 8A partitioned by the protruding portions 13. In a manner similar, the second fertilized egg is put into the well 8 in such a manner as to be settled on one of the four portions of the bottom 8A, the one being different from the portion of the bottom 8A in which the first fertilized egg is settled. The remaining two fertilized eggs are each settled on one of the other partitioned portions of the bottom 8A by a similar operation.

Each of the fertilized eggs is settled on one of the portions of the bottom 8A partitioned by the protruding portions 13, and thus, the fertilized eggs do not come into contact with one another in the well 8.

Each of the fertilized eggs is left to stand in the well 8 for approximately 15 minutes, and at this time, the cell freezing tool having a flat plate-like shape is placed in the groove 12.

Subsequently, one of the fertilized eggs and the equilibrium solution are sucked in by a capillary and put into the well 9. At the time of this operation, the equilibrium solution remaining in the capillary is discarded in the waste-liquid portions 11. After that, the capillary is rinsed out with the vitrification solution in the well 9 and the well 10, and the fertilized egg and the vitrification solution are sucked in by the capillary. The fertilized egg, which has been sucked in, is put into the well 10.

The vitrification solution in the well 10 is stirred by the capillary, and the state of the fertilized egg is checked. After that, the capillary is rinsed out with the vitrification solution in the well 10. The fertilized egg sucked in by the capillary is dropped onto an end of the cell freezing tool and frozen by using liquid nitrogen.

The above operation is performed on each of the fertilized eggs settled on the well 8, and the four fertilized eggs are frozen by using the single instrument 1.

Advantageous effects of the instrument 1 according to the present embodiment will now be described.

A major feature of the instrument 1 according to the present embodiment is the protruding portions 13 that are provided in order to partition the bottom 8A of the well 8 into a plurality of portions.

In the instrument 1 according to the present embodiment, by providing the two protruding portions 13 on at least the bottom 8A of the well 8, the bottom 8A of the well 8 is partitioned by the protruding portions 13. As a result, the bottom 8A is divided into the four portions, and each fertilized egg can be settled on one of the four portions of the bottom 8A.

As described above, by using the instrument 1 according to the present embodiment, the single instrument 1 is enough to perform the operation of freezing four fertilized eggs, and thus, fertilized eggs can be promptly handled compared with the case where a single instrument (a plate main body) is used for freezing a single fertilized egg. In addition, the number of instruments to be used, the amount of an equilibrium solution to be used, and the amount of a vitrification solution to be used can be reduced, and a fertilized egg can be frozen at a lower cost.

Since the raised portions 13A are formed on the bottom 8A, in the bottom 8A, the recesses 13B are formed at positions a short distance away from their respective protruding portions 13. As a result, fertilized eggs that are put into the well 8 are settled into the recesses 13B and thus, the protruding portions 13 do not become hindrances in observation, and the fertilized eggs can be observed with favorable visibility. In addition, since the fertilized eggs are settled in the recesses 13B, the fertilized eggs can be promptly checked by aligning a lens of a microscope with the positions of the recesses 13B.

In the instrument 1 according to the present embodiment, the protruding portions 13 are each provided so as to extend from the bottom 8A to the side wall 8B. As a result, the protruding portions 13 serve as guiding portions, and each fertilized egg that is put into the well 8 is guided, in the equilibrium solution, to a target portion of the bottom 8A. Accordingly, each fertilized egg may easily be guided to a target portion of the bottom 8A, and the operability is improved.

In the instrument 1 according to the present embodiment, the plate main body 2 includes the plurality of waste-liquid portions 11. When an operation of freezing fertilized eggs is performed, a waste liquid that is generated as a result of, for example, a rinsing process can be discarded into the waste-liquid portions 11. Since each of the waste-liquid portions 11 is formed at a position close to a corresponding one of the wells 8 to 10, an operation of discarding the waste liquid can be smoothly performed.

A modification of the shape of the bottom 8A of the well 8 and a modification of the shape of each of the protruding portions 13 will now be described.

Figure 5:
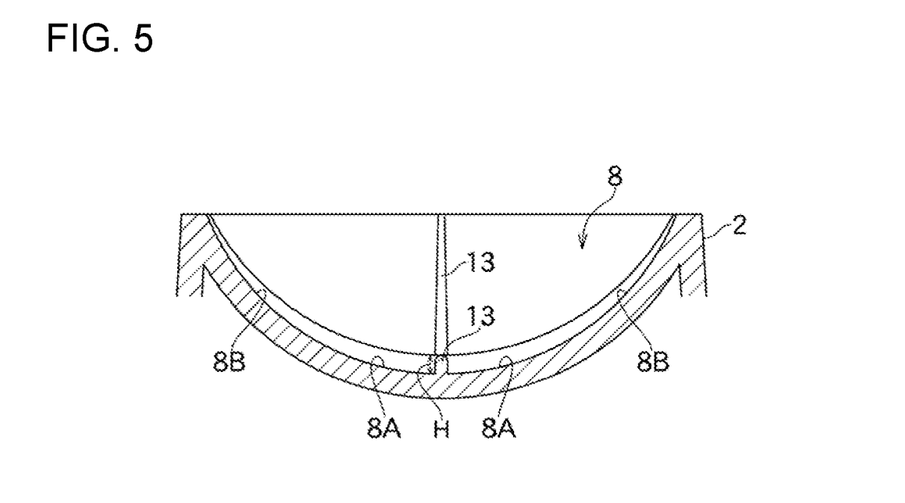
FIG. 5 is an enlarged cross-sectional view illustrating a modification of a well of the instrument according to the embodiment of the present disclosure.
Figure 6:
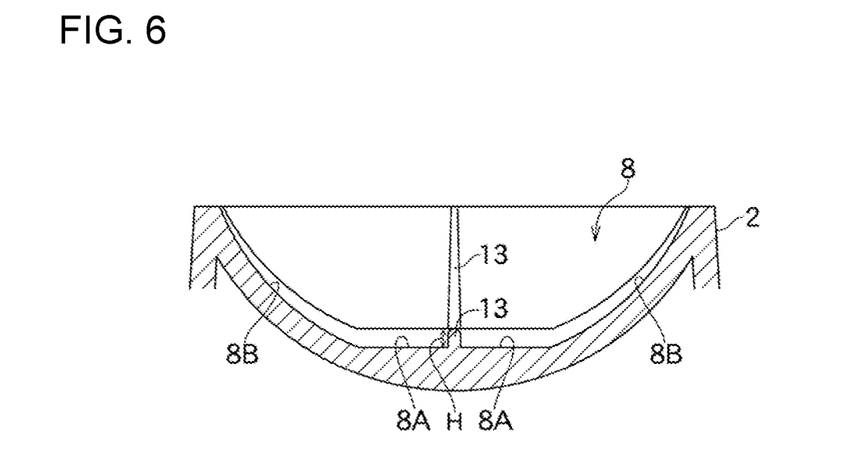
FIG. 6 is an enlarged cross-sectional view illustrating another modification of the well of the instrument according to the embodiment of the present disclosure.

As illustrated in FIG. 5, only the protruding portions 13 may be formed on the curved bottom 8A of the well 8 without forming the raised portions 13A on the bottom 8A. In this case, the bottom 8A and the side wall 8B are formed so as have the same curvature. In addition, as illustrated in FIG. 6, the bottom 8A may be formed into a flat shape. Regardless of which shape is employed, an operation of freezing a plurality of fertilized eggs can be performed by using the single well 8.

Figure 7A:
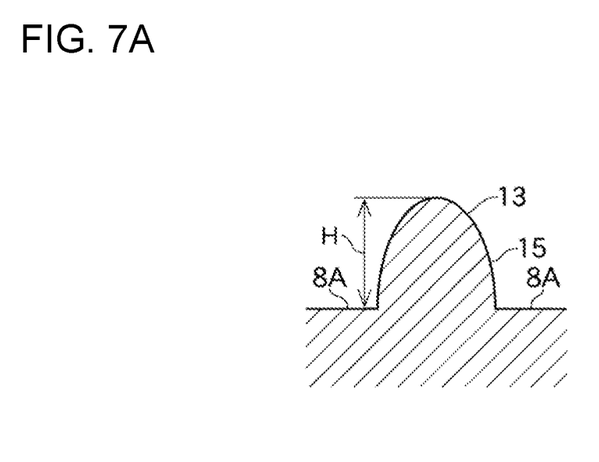
FIG. 7A is a cross-sectional view of a protruding portion of the instrument, having a semielliptical cross section according to the embodiment of the present disclosure.
Figure 7B:
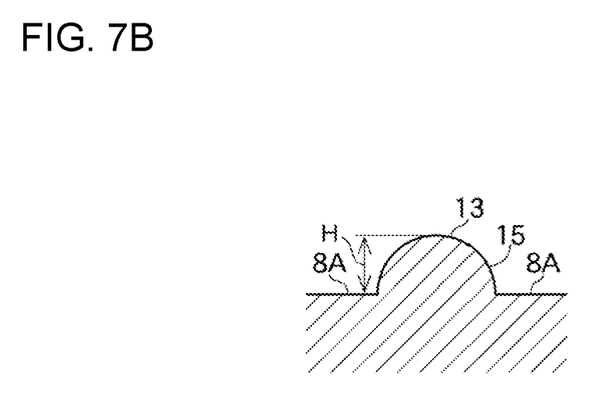
FIG. 7B is a cross-sectional view of a protruding portion of the instrument, having a semicircular cross section according to the embodiment of the present disclosure.
Figure 7C:
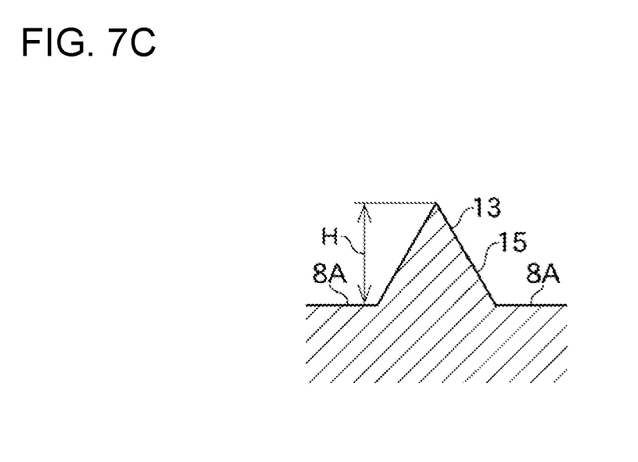
FIG. 7C is a cross-sectional view of a protruding portion of the instrument, having a triangular cross section according to the embodiment of the present disclosure.

As illustrated in FIG. 7, the protruding portions 13 can have, in the lateral direction, a semielliptical cross section (FIG. 7A), a semicircular cross section (FIG. 7B), or a triangular cross section (FIG. 7C) and can each have an inclined surface 15 that is inclined in a direction from an upper end to a lower end thereof. As a result of each of the protruding portions 13 having the inclined surface 15, for example, even if a fertilized egg is settled on the upper end of one of the protruding portions 13, the fertilized egg can be settled onto the bottom 8A by moving on the corresponding inclined surface 15.

In addition, in the case where the upper end of each of the inclined surfaces 15 has a curved semielliptical spherical shape or a spherical shape, when a fertilized egg comes into contact with the end of one of the inclined surfaces 15, the fertilized egg can be settled onto the bottom 8A without being damaged.

As described above, the instrument 1 according to the present embodiment includes the plate main body 2 having the well 8 into which the equilibrium solution is injected and can be used at a stage before a cell is frozen, and the well 8 has the bottom 8A, which is formed in a curved shape, and the inner peripheral wall 8B, which has a curved shape and which is formed so as to be contiguous to the bottom 8A. In addition, the plurality of protruding portions 13 for partitioning the bottom 8A and the inner peripheral wall 8B into a plurality of portions is provided in such a manner as to extend from the center of the well 8 along the bottom 8A and the inner peripheral wall 8B, and portions of the bottom 8A partitioned by the protruding portions 13 communicate with their respective portions of the inner peripheral wall 8B partitioned by the protruding portions 13. Furthermore, the raised portions 13A are formed so as to extend from the protruding portions 13 toward the bottom 8A, so that the recesses 13B are formed in the partitioned portions of the bottom 8A, and cells are settled into the recesses 13B.

Although the present embodiment has been described above, the configurations described in the above embodiment can be selected or suitably changed to other configurations within the gist of the present invention. For example, in the present embodiment, although the case has been described in which the protruding portions 13 are provided, a plurality of fertilized eggs can be handled without causing them to come into contact with each other by providing a partition plate in the well 8.

In addition, in the present embodiment, although the case has been described in which each of the protruding portions 13 is formed so as to extend from the bottom 8A to the side wall 8B, the protruding portions 13 can be provided only on the bottom 8A as long as they can partition the bottom 8A into a plurality of portions.

The inner peripheral walls of the wells 8 to 10 may be curved or may be tapered. In addition, in the case where the instrument 1 is used at a stage before a fertilized egg or an unfertilized egg is frozen, the number of wells is not limited to three as long as a well into which an equilibrium liquid is dispensed and a well into which a vitrification solution is dispensed are provided.

Note that, depending on a cell to be operated, the plate main body 2 of the instrument 1 may include only the well (first well) 8.

In addition, the cross-sectional shapes of the protruding portions 13 in the lateral direction are not limited to those mentioned in the embodiment and may be, for example, a quadrangular shape, a trapezoidal shape, or a shape in which the two sides of the upper end portion are recurved. Furthermore, the groove 12 of the plate main body 2 can be shaped so as to follow the shape of a holding portion of the cell freezing tool, which is to be placed in the groove 12, and for example, in the case where the holding portion of the cell freezing tool has a hexagonal shape, the groove 12 can have a hexagonal shape.

REFERENCE SIGNS LIST 1 instrument
2 plate main body (main body portion)
3 cover member
4 front wall
5 rear wall
6 left side wall
7 right side wall
8 well (first well)
8A bottom
8B side wall (inner peripheral wall)
9 well (second well)
10 well (third well)
11 waste-liquid portion (recess for waste liquid)
12 groove
13 protruding portion
13A raised portion
13B recess
15 inclined surface
L1, L2 length
H height
X transverse direction
Y depth direction
Z vertical direction

The invention claimed is:

1. An instrument that includes a main body portion having a first well and that is used when cells are operated,
wherein the first well has a bottom that is formed in a curved shape and a curved inner peripheral wall that is contiguous to the bottom,
wherein a plurality of protruding portions for partitioning the bottom and the inner peripheral wall into a plurality of portions is provided along the bottom and the inner peripheral wall,
wherein recesses are formed in partitioned portions of the bottom by forming raised portions in such a manner that each of the raised portions extends from one of the protruding portions to the bottom, and the cells are settled in the recesses, and
wherein the height of each of the protruding portions gradually increases from the inner peripheral wall to the bottom.

2. The instrument according to claim 1,
wherein the protruding portions are each provided in such a manner as to extend from the center of the first well along the bottom and the inner peripheral wall.

3. The instrument according to claim 2,
wherein the bottom partitioned by the protruding portions and the inner peripheral wall partitioned by the protruding portions communicate with each other.

4. The instrument according to claim 1,
wherein the bottom partitioned by the protruding portions and the inner peripheral wall partitioned by the protruding portions communicate with each other.

5. The instrument according to claim 1,
wherein the bottom and the inner peripheral wall are each partitioned into four portions by arranging the plurality of the protruding portions in such a manner that the protruding portions cross each other at the center of the bottom.

6. The instrument according to claim 1,
wherein each of the protruding portions has a curved end and an inclined surface that extends from an upper end of the protruding portion to a lower end of the protruding portion.

7. The instrument according to claim 1,
wherein each of the protruding portions has a height of 100 µm to 1,000 µm.

8. The instrument according to claim 1,
wherein the main body portion has a second well that is formed adjacent to the first well, and an equilibrium solution and a vitrification solution are respectively injected into the first well and the second well,
wherein the protruding portions are formed only in the first well, and
wherein the instrument is used at a stage before the cells are frozen.

9. The instrument according to claim 8,
wherein a waste-liquid portion for discarding a liquid injected in the first well or the second well is formed in the main body portion.

* * * * *